United States Patent [19]

Opekun, Jr. et al.

[11] Patent Number: 5,140,993

[45] Date of Patent: Aug. 25, 1992

[54] DEVICE FOR COLLECTING A BREATH SAMPLE

[75] Inventors: Antone R. Opekun, Jr., Pearland; Peter D. Klein, Houston, both of Tex.

[73] Assignee: Baylor College of Medicine, Houston, Tex.

[21] Appl. No.: 813,646

[22] Filed: Dec. 27, 1991

[51] Int. Cl.5 .............................................. A61B 5/097
[52] U.S. Cl. ..................................... 128/730; 422/84
[58] Field of Search ............... 128/719, 727, 728, 730, 128/716; 422/84; 73/23.3, 863.23, 863.81, 863.86, 864.63

[56] References Cited

U.S. PATENT DOCUMENTS 2,591,691 4/1952 Forrester ............................. 422/84

Primary Examiner—Lee S. Cohen
Assistant Examiner—Brian L. Casler
Attorney, Agent, or Firm—Dodge, Bush, Moseley & Riddle

[57] ABSTRACT

In accordance with illustrative embodiments of the present invention as disclosed herein, a breath sample collecting device includes a flexible plastic bag having a mouthpiece and inlet valve assembly connected adjacent one end of the bag, and a sample transfer assembly connected adjacent the other end of the bag. The transfer assembly has a sleeve attached to a neck on the bag, such sleeve having an inner end wall which mounts a hollow needle having a sharp tip on its outer end in a manner such that the tip is within the bore of the sleeve to prevent accidental stick injuries. A rubber boot which closes the tip, and an elastomer stopper on an associated transfer device, are selectively pierced by the needle tip in response to compressive force to permit transfer of a breath sample from the bag to such associated device.

8 Claims, 1 Drawing Sheet

DEVICE FOR COLLECTING A BREATH SAMPLE

FIELD OF THE INVENTION

This invention relates generally to breath sampling equipment and particularly to a breath sample collecting bag having new and improved inlet and sample transfer assemblies which make the device safe and reliable in use.

BACKGROUND OF THE INVENTION

There is a need primarily in the medical field for a reliable device which allows patients, research subjects, physicians and allied health personnel to collect an expired breath sample for testing, analysis and related diagnosis. The principle constituents of a breath sample that are of interest in this field are the tracer or isotopically labeled metabolites derived from protein, carbohydrates, fats, amino acids, nucleic acids, drugs, and microscopic organisms, to mention but a few. The metabolites would be carbon dioxide and hydrogen, in addition to the oxygen and nitrogen gases that normally are present in the air. Prior sample collecting devices of which applicants are aware have a number of shortcomings. They often leak or have flaws which result in loss of the sample. Moreover, some devices require manipulation of an unprotected hypodermic needle in order to transfer all or a part of the sample to another container or to an analyzer machine, which can result in accidental and painful needle sticks.

An object of the present invention is to provide a new and improved breath sampling device which is constructed in a manner such that it is safe and reliable in use.

Another object of the present invention is to provide a new and improved breath sampling assembly that has a propensity to not leak, and thus holds the sample longer.

Still another object of the present invention is to provide a new and improved device of the type described which provides consistent and safe sample transfer.

SUMMARY OF THE INVENTION

These and other objects are attained in accordance with the present invention through the provision of a breath collecting device which comprises a flexible, inflatable plastic bag having an inlet assembly that includes a valve which is opened during insufflation and closed when exhaling is stopped. The valve can be a check valve that permits gas flow only toward the inside of the bag, or a manually operated stop-cock valve. The valve body provides a mouthpiece through which the bag is inflated. An outlet assembly on the bag by which all or a portion of the sample is transferred to another device includes a neck, a sleeve member having an inner end wall mounted in said neck, and a hollow transfer needle mounted on said end wall in a manner such that its sharp tip is located within the bore of the sleeve member. The needle and its tip normally are covered by an elastomer boot which prevents escape of the breath sample. However when a container having a rubber stopper on its outer end is inserted into the sleeve member, the tip of the needle pierces the boot and the stopper to permit removal of all or a part of the breath sample from the bag. The mounting of the needle within the bore of the sleeve member prevents accidental injury on account of needle sticks, because the sleeve member provides a protective cover over the needle. The device can be readily disassembled and reassembled for reuse where a series of samples needs to be analyzed.

BRIEF DESCRIPTION OF THE DRAWINGS

The present invention has other objects, features and advantages which will become more clearly apparent in connection with the following detailed description of preferred embodiments thereof, taken in conjunction with the appended drawings in which.

DETAILED DESCRIPTION OF PREFERRED EMBODIMENTS

Figure 1:
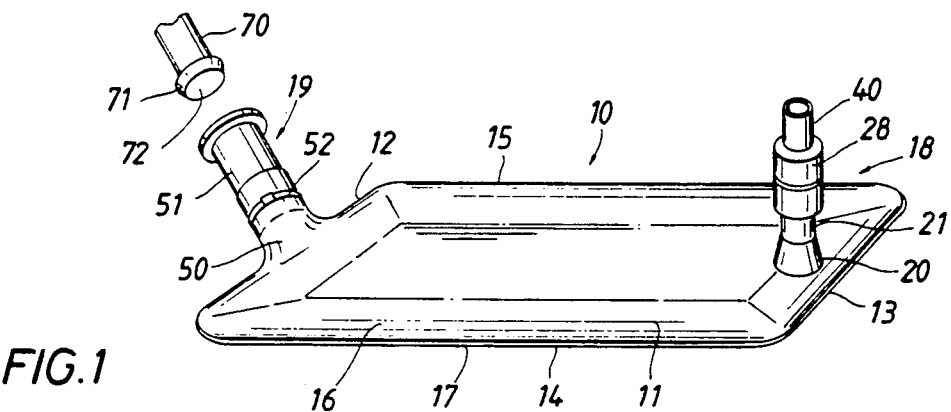
FIG. 1 is a isometric view of the breath sample collection device of the present invention.

Referring initially to FIG. 1, a breath sample collection device 10 includes a generally rectangular, inflatable bag 11 that preferably is made of an impervious, flexible, medical-grade plastic material such as polyvinyl chloride. For adult use the bag 11 can have a fully inflated volume, without stretching, of about 2 liters, although the volume can be somewhat less for pediatric use. The end seams 12, 13, the side seams 14, 15 and front and back panels 16, 17 of the bag 11 are formed so that it is essentially flat prior to use, and can be folded up for storage in another plastic bag.

Figure 2:
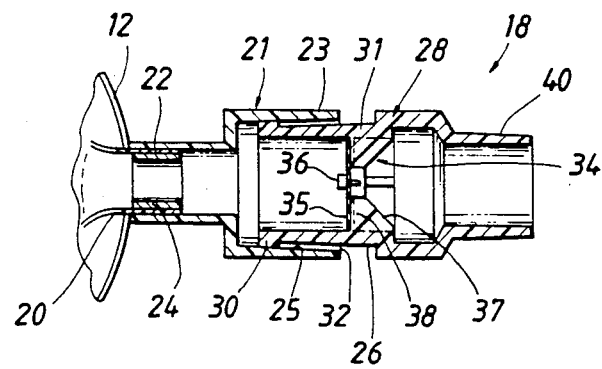
FIG. 2 is an enlarged, fragmentary, cross-sectional view of the bag inlet construction taken on line 2—2 of FIG. 1.

The inlet mechanism 18 through which a patient exhales in order to insufflate the bag 11 with a breath sample is shown in detail in FIG. 2. A conical neck 20 which communicates with the interior of the bag 11 is formed at a suitable location, for example near the end seam 13. An adapter 21 having a smaller diameter inner section 22 and a larger diameter outer section 23 is fitted onto the neck 20, and a tubular insert 24 is forced inside the neck to secure the parts together. The outer section 23 has an inner bore 25 that flares slightly outward, and receives the inner section 26 of a tubular valve body 28. The inner end of the section 26 is provided with an outwardly directed flange 30 that fits tightly in the bore 25 when the parts are pushed together, but not with such force as to prevent easy manual disassembly to permit deflation of the bag 11 after a sample has been transferred. This feature allows subsequent reuse of the device 10 for serial sampling. The outer surface 31 of the section 26 can be tapered outwardly as shown so that it engages the inner edge 32 of the adapter section 23 to stabilize the parts in a coaxial relationship and to form a gas-tight seal.

The valve body 28 is formed with an internal spider 34 which provides an inwardly facing support for a disc-shaped membrane 35 that functions as a one-way check valve. The membrane 35 has a central hole that enables it to be captured by a head 36 on the center part of the spider 34. The spider 34 has reinforcing ribs 37 at angularly spaced positions, as well as angularly spaced projections 38. When a fluid seeks to flow to the left in FIG. 2, the outer margins of the membrane 35 move away from the spider 34 to permit flow between its legs. However when flow is stopped, the membrane 35 relaxes against the spider 34 to prevent reverse flow to the right. The valve body 28 has an outer section 40 which provides a mouthpiece through which the patient exhales breath to fill the bag 11 via the check valve 35 and the adapter 21.

Figure 3:
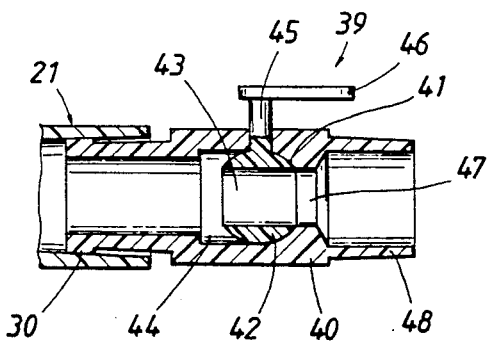
FIG. 3 is a view similar to FIG. 2 of an alternative inlet assembly.

As an alternative inlet valve arrangement, the one-way check valve assembly 28 can be replaced by a stop-cock valve assembly 39 as shown in FIG. 3. Here the tubular valve body 40 has an annular spherical seat 41 formed to face inwardly, and a ball valve 42 having a central bore 43 is rotatably mounted in the cavity 44. The ball valve 42 has a stem 45 which extends through a side opening in the body to the outside, where its outer end is fixed to a handle 46. In one position of the handle 46 the bore 43 is lined up with the flow passage 47 to admit breath into the bag 11, and in another position the bore is misaligned so that the outer spherical surface of the ball engages the seat 41 to prevent outward flow. The tubular outer end section 48 of the valve body 40 provides the mouthpiece through which the patient can insufflate the bag 11. Once the bag 11 is filled with a breath sample, the patient or an assistant can close the valve element 42 to trap the sample in the bag.

Figure 4:
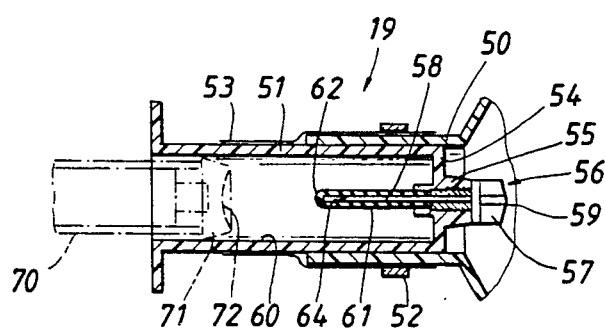
FIG. 4 is an enlarged cross-sectional view showing the outlet assembly of the bag.

FIG. 4 shows in enlarged detail the construction of the outlet assembly 19 by which a sample of the bag's content can be is transferred to another sealed enclosure or directly to a transfer tube which leads to an analyzer machine. A neck portion 50 of the bag 11 is formed to communicate with its interior, for example near or at the opposite end seam 12. The inner portion of a rigid static sleeve member 51 is positioned within the neck 50 and held by a ratchet-type clamp 52 or the like. A layer of tape 53 can be positioned to overlie the neck 50 and a portion of the sleeve member 51 beyond the end thereof, such tape extending underneath the clamp 52 and arranged to further insure against leakage. The sleeve member 51 has an inner end wall 54 that forms a threaded hub 55. A portion of a hypodermic needle assembly 56 has a boss 57 which is threaded into the hub 55 in a manner such that the needle or cannula 58 extends outwardly into the bore 60 of the sleeve member 51. The inner end 59 of the needle 58 remains flush with the inner end of the hub 57 to prevent any possibility of accidental puncture of the bag 11. A small rubber boot 61 having a closed outer end 62 fits tightly over the outer portion of the needle 58, as shown, to prevent outward gas flow and to prevent any substances from entering the bag 11 via the needle. The outer end of the needle 58 is cut on a bias to provide a sharp tip 64. The boot 61 is sufficiently pliable to allow the tip 64 to pierce its outer end 62 when compressed. The boot 61 resumes its normal position shown in FIG. 4 and reseals the bag 11 from the ambient atmosphere when the compressive force is removed.

OPERATION

In use, the breath sample collection device 10 is made and assembled as shown in the drawings, and can be folded and stored in a relatively flat condition in a sterile plastic enclosure. To take a breath sample, the device 10 is removed from the enclosure and folded out flat, and the patient takes a deep breath and then places the mouthpiece 40 or 48 in the mouth. In case the stop-cock valve assembly 39 is used, either the patient or a medical assistant opens the valve element 42 by hand so that the patient can exhale through the passage 47 and inflate the bag 11. As the patient exhales, the bag 11 gradually fills and eventually expands substantially completely. Of course it is not necessary to completely inflate the bag 11 when the patient does not have sufficient lung capacity to do so, or where a lesser sample volume is sufficient. In any event the valve element 42 is manually closed when sample taking is completed. Of course where the one-way check valve 35 shown in FIG. 2 is employed, any reverse flow is automatically prevented by the membrane 35. The non-porous or impervious nature of the bag 11 preserves the entire sample, which cannot leak from the bag due to the positive closure provided by the inlet valve assemblies and to the closure of the outlet needle 58 by the rubber boot 61.

In order to transfer all or part of the sample to a suitable device such as a glass sample tube 70 shown in phantom lines in FIGS. 1 and 4, or to a hose that leads to an analyzer machine, the rubber stopper 71 that closes the outer end of the tube is pushed by the tube into the bore 60 of the sleeve member 51. When the outer end wall 72 of the stopper 71 encounters the outer end 62 of the rubber boot 61, both the said end wall 62 and the wall 72 of the stopper are pierced by the tip 64 so that the tip and the outer end portion of the needle 58 becomes positioned within the glass tube 70 to the rear of the stopper 71. The bore of the needle 58 then provides a transfer connection between the interior of the bag 11 and the tube 70 to enable a breath sample to be transferred, for example, by slightly or totally collapsing the bag 11 by hand. Then the stopper 71 and the outer end of the tube 70 are pulled out of the bore of the sleeve member 51, and the pierced hole in the stopper collapses and closes to contain the transferred sample. As noted above, the end portion 62 also reseals the needle 38. This same type of connection can be used to transfer the sample directly to a flexible plastic tube which leads to an analyzer machine that operates to determine, for example, the relative percentages of each metabolite of interest, such as carbon dioxide, hydrogen, oxygen and nitrogen, as well as the derivative source of such metabolites. Where one or more of these metabolites has a percentage that is out of the normal range or otherwise suspect, then further diagnostic work can be done to determine the cause of the abnormality.

When the ball valve assembly 39 is used as an intake valve instead of the one-way check valve 35 shown in FIG. 2, the valve element, which normally is closed, is opened manually after the mouthpiece has been positioned in the mouth of the patient. After the bag 11 has been insufflated, the valve 39 is closed manually to trap the breath sample in the bag. The present invention allows easy deflation and transfer of any unused portion of the breath sample, as well as easy reassembly for reuse and collection of several samples.

It now will be recognized that a new and improved breath sample collection device has been disclosed which meets the various objects, and which has the advantages and features of, the present invention. Since certain changes or modifications may be made in the disclosed embodiments without departing from the inventive concepts involved, it is the aim of the appended claims to cover all such changes and modifications falling within the true spirit and scope of the present invention.

What is claimed is:

1. A device for use in collecting a breath sample, comprising: a flexible bag made of a medical grade, impervious plastic; inlet means adjacent one end of the bag by which it can be insufflated by a patient, said inlet means including a mouthpiece providing an inlet passage, and valve means for opening and closing said inlet passage; and outlet means adjacent the opposite end of said bag for safely transferring at least a portion of said sample to an external container, said outlet means including a sleeve member having a bore and an inner end wall, and a needle assembly mounted on said inner end wall, a needle of said assembly having a bore and a tip and extending outward into the bore of said sleeve member in a manner such that its tip is positioned within said bore of the sleeve member means on said needle for covering said tip and for closing the bore of said needle, said tip being arranged to pierce said covering means and a wall of an associated external transfer means to thereby communicate the interior of said bag with said associated external transfer means.

2. The device of claim 1 further including a flexible neck having a bore and having its inner end joined to said bag, an inner portion of said sleeve member being received in the bore of said neck, and means for clamping said neck on said sleeve member to prevent fluid leakage therebetween.

3. The device of claim 1 wherein said valve means includes a one-way check valve element which permits flow only into the interior of said bag.

4. The device of claim 3 further including neck means on said bag having a bore in communication with the said interior of said bag; and adapter means for coupling said neck means to said valve means.

5. The device of claim 4 wherein said adapter means comprises a sleeve having an internal bore surface that tapers outwardly, said valve means including a body with an external flange that slides into said sleeve and fits tightly within said internal bore surface.

6. The device of claim 5 wherein said adapter means comprises a sleeve having an internal bore surface that tapers outwardly, said valve means including a body with an external flange that slides into said sleeve and fits tightly within said internal bore surface.

7. The device of claim 1 wherein said valve means includes a valve element that can be moved manually between open and closed positions.

8. The device of claim 7 further including neck means on said bag having a bore in communication with the said interior of said bag; and adapter means for coupling said neck means to said valve means.

* * * * *